（12） United States Patent
Parker et al.

(10) Patent No.: US 7,400,918 B2
(45) Date of Patent: Jul. 15, 2008

(54) MEASUREMENT OF BLOOD OXYGEN SATURATION

(75) Inventors: Dawood Parker, Whitland (GB);
Michael J. Higgins, Huntington Beach, CA (US)

(73) Assignee: Edwards Lifesciences, Irvine, CA (US)

( * ) Notice: Subject to any disclaimer, the term of this patent is extended or adjusted under 35 U.S.C. 154(b) by 404 days.

(21) Appl. No.: 10/950,257

(22) Filed: Sep. 24, 2004

(65) Prior Publication Data

US 2005/0119543 A1     Jun. 2, 2005

Related U.S. Application Data

(63) Continuation-in-part of application No. 09/743,206, filed as application No. PCT/GB99/02127 on Jul. 2, 1999, now Pat. No. 6,990,365, and a continuation-in-part of application No. 09/762,923, filed as application No. PCT/GB99/02510 on Jul. 30, 1999, now Pat. No. 6,842,635.

(30) Foreign Application Priority Data

| Jul. 4, 1998 | (GB) | ................................ 9814464.5 |
| Aug. 13, 1998 | (GB) | ................................ 9817552.4 |
| Nov. 13, 1998 | (GB) | ................................ 9824899.0 |
| Nov. 19, 1998 | (GB) | ................................ 9825243.0 |
| Feb. 25, 1999 | (GB) | ................................ 9904232.7 |

(51) Int. Cl.
*A61B 5/00* (2006.01)
(52) U.S. Cl. ...................................... 600/323; 600/322
(58) Field of Classification Search .................. 600/322, 600/323, 331, 336
See application file for complete search history.

(56) References Cited

U.S. PATENT DOCUMENTS

| 4,942,877 | A | * | 7/1990 | Sakai et al. .................. 600/323 |
| 5,372,136 | A | | 12/1994 | Steuer et al. |
| 5,482,036 | A | | 1/1996 | Diab et al. |
| 5,490,505 | A | | 2/1996 | Diab et al. |
| 5,499,627 | A | | 3/1996 | Steuer et al. |
| 5,553,615 | A | | 9/1996 | Carim et al. |
| 5,685,299 | A | | 11/1997 | Diab et al. |
| 5,706,208 | A | | 1/1998 | Osten et al. |
| 5,729,333 | A | | 3/1998 | Osten et al. |
| 5,769,785 | A | | 6/1998 | Diab et al. |
| 5,803,908 | A | | 9/1998 | Steuer et al. |
| 5,817,007 | A | | 10/1998 | Fodgaard et al. |

(Continued)

FOREIGN PATENT DOCUMENTS

WO     WO 93/13706     7/1993

(Continued)

*Primary Examiner*—Eric F. Winakur
*Assistant Examiner*—Etsub D Berhanu

(57) ABSTRACT

Oxygenation of a subject's blood is determined by sensing an absorption spectrum of light directed either invasively or non-invasively into the blood, and then calculating an oxygenation value by evaluating a cost function of the remitted spectrum relative to at least two pre-determined reference absorption spectra representing different, known levels of blood oxygenation. The source of light preferably uses stable, long-life, white LEDs, in which case white-balancing of the remitted spectrum can be accomplished by pre-determining and storing the spectrum of the LEDs, one time for all, and then adjusting the remitted spectrum accordingly to compensate for deviations of the LED spectrum from the constant ideal.

24 Claims, 2 Drawing Sheets

U.S. PATENT DOCUMENTS

| | | | |
|---|---|---|---|
| 5,842,981 | A | 12/1998 | Larsen et al. |
| 5,891,024 | A | 4/1999 | Jarman et al. |
| 5,922,607 | A | 7/1999 | Bernreuter |
| 6,006,119 | A | 12/1999 | Soller et al. |
| 6,036,642 | A | 3/2000 | Diab et al. |
| 6,104,938 | A | 8/2000 | Huiku et al. |
| 6,122,535 | A | 9/2000 | Kaestle et al. |
| 6,163,715 | A | 12/2000 | Larsen et al. |
| 6,206,830 | B1 | 3/2001 | Diab et al. |
| 6,219,565 | B1 | 4/2001 | Cupp et al. |
| 6,226,540 | B1 | 5/2001 | Bernreuter |
| 6,263,222 | B1 | 7/2001 | Diab |
| 6,266,546 | B1 | 7/2001 | Steuer et al. |
| 6,397,093 | B1 | 5/2002 | Aldrich |
| 6,415,233 | B1 | 7/2002 | Haaland |
| 6,501,975 | B2 | 12/2002 | Diab et al. |
| 6,526,298 | B1 | 2/2003 | Khalil et al. |
| 6,526,299 | B2 | 2/2003 | Pickard |
| 6,606,509 | B2 | 8/2003 | Schmitt |
| 6,650,917 | B2 | 11/2003 | Diab et al. |
| 6,662,031 | B1 | 12/2003 | Khalil et al. |
| 6,700,661 | B1 | 3/2004 | Cadell et al. |
| 6,842,635 | B1 * | 1/2005 | Parker ................... 600/323 |
| 2001/0005773 | A1 | 6/2001 | Larsen et al. |
| 2001/0029326 | A1 | 10/2001 | Diab et al. |
| 2002/0038079 | A1 | 3/2002 | Steuer et al. |
| 2002/0086432 | A1 | 7/2002 | Tam et al. |
| 2002/0095078 | A1 * | 7/2002 | Mannheimer et al. ....... 600/323 |
| 2002/0137993 | A1 | 9/2002 | Pickard |
| 2003/0009090 | A1 | 1/2003 | Jeon et al. |
| 2003/0097049 | A1 | 5/2003 | Diab et al. |
| 2003/0220576 | A1 | 11/2003 | Diab |
| 2003/0236647 | A1 | 12/2003 | Yoon et al. |
| 2004/0015060 | A1 | 1/2004 | Samsoondar et al. |
| 2004/0054268 | A1 | 3/2004 | Esnaliev et al. |

FOREIGN PATENT DOCUMENTS

| | | | |
|---|---|---|---|
| WO | WO 97/27800 | | 8/1997 |
| WO | WO 00/09004 | * | 2/2000 |

* cited by examiner

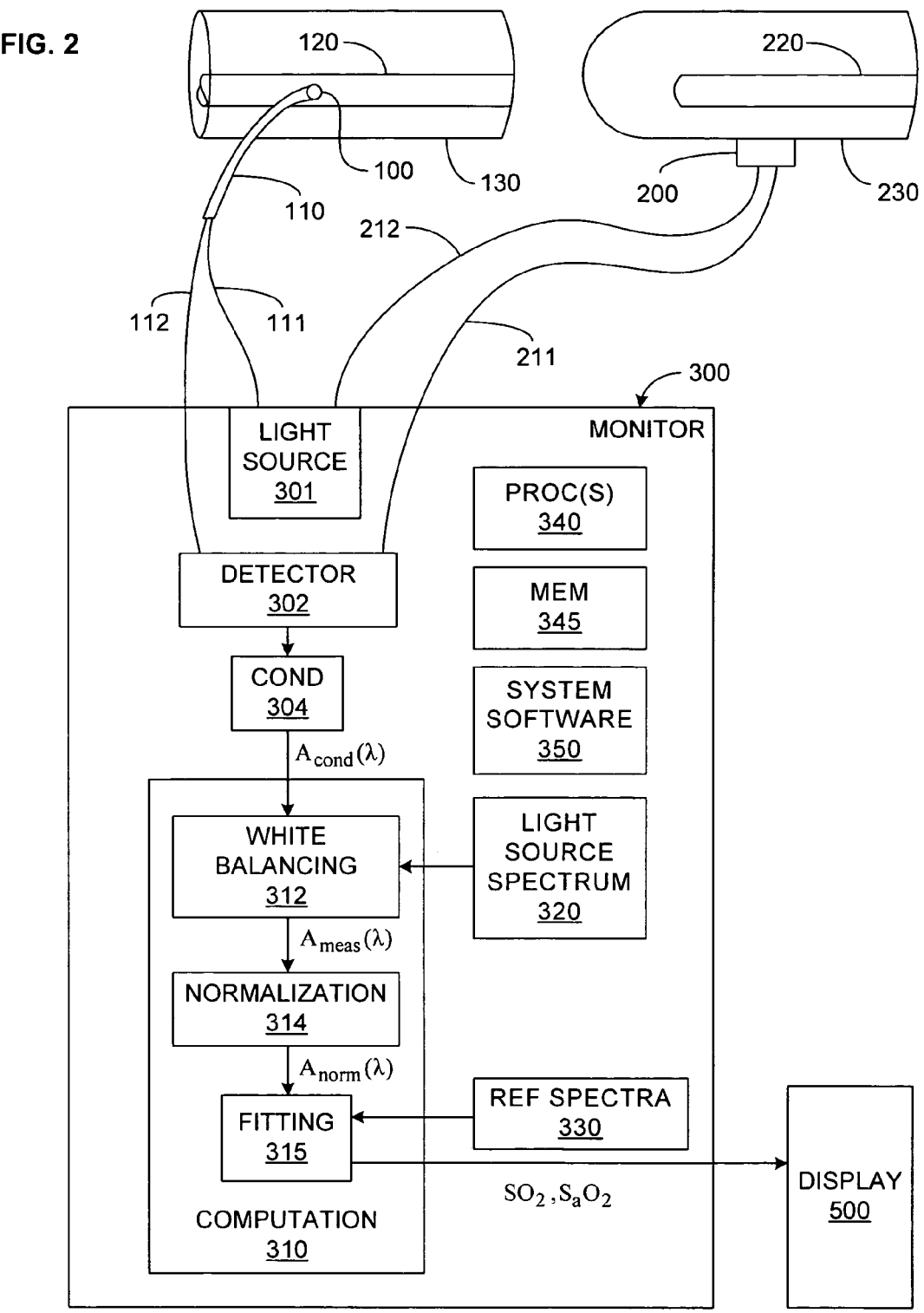

MEASUREMENT OF BLOOD OXYGEN SATURATION

CROSS-REFERENCE TO RELATED APPLICATIONS

This application claims priority of and is a continuation-in-part (CIP) of U.S. patent application Ser. No. 09/743,206 filed 15 Mar. 2002 and now U.S. Pat. No. 6,990,365, which is a national stage application claiming priority of international (PCT) patent application no. PCT/GB99/02127, filed 2 Jul. 1999, which in turn claims priority of Great Britain Patent Application No. 9825243.0, filed 19 Nov. 1998, Great Britain Patent Application No. 9824899.0, filed 13 Nov. 1998, and Great Britain Patent Application No. 9814464.5, filed 4 Jul. 1998.

This application also claims priority of and is a CIP of U.S. patent application Ser. No. 09/762,923 filed 16 Apr. 2001, now U.S. Pat. No. 6,842,635, which is a national stage application claiming priority of international patent application no. PCT/GB99/02510, filed 30 Jul. 1999, herein incorporated by reference, which in turn claims priority of both Great Britain Patent Application No. 9817552.4, filed 13 Aug. 1998, herein incorporated by reference, and Great Britain Patent Application No. 9904232.7, filed 25 Feb. 1999, herein incorporated by reference.

This application also claims priority of Great Britain Patent Application No. 0322545.5, filed Sep. 26, 2003, herein incorporated by reference.

BACKGROUND OF THE INVENTION

1. Field of the Invention

This invention relates to a method and a system implementation for determining the oxygen saturation ($SO_2$) of blood in a blood vessel or body organ. The invention may employ invasive or non-invasive measurement techniques and is suitable for determining blood oxygen saturation in patients in any context, for example, central venous $SO_2$ monitoring, pulmonary artery $SO_2$ monitoring, extracorporeal $SO_2$ monitoring, amputation level assessment, free-flap $SO_2$ monitoring, etc.

2. Description of the Related Art

The standard way to measure blood oxygen saturation in a patient is to direct light into or through the blood, to measure the intensity of the light at either discrete wavelengths or over a substantially continuous spectral range after transmission through or reflection by the blood, and then to calculate $SO_2$ as a function of the measured intensity values. Such devices are described, for example, in International Patent Application No WO94/03102.

Many factors reduce the accuracy of known $SO_2$ monitors. Beginning with the light source itself, it must be able to produce light at a well-defined wavelength, or over a well-defined wavelength range, and it should do so stably over the life of the measurement instrument—there is no point measuring light absorption at a wavelength that is not produced with enough intensity to allow for a useful range of detection.

Getting the light to blood is also affected by various irregularities. When the light is directed into the blood using a non-invasive device such as a finger or ear lobe cuff, for example, inhomogeneities and irregularities in the body tissue between the light-generating device and the blood can influence light transmission in sometimes hard-to-estimate ways, which have nothing to do with the degree of blood oxygen saturation.

One irregularity that degrades the accuracy of most non-invasive monitors is patient motion, that is, motion artifact, which leads to a change in the path length of the light through the biological tissue and hence to a variation in the intensity of the detected transmitted or reflected light. This problem is in fact so great that it can render these devices inoperative for long periods of time. The problem is particularly severe in critical health care applications, were continuous monitoring is essential.

Generally, medical practitioners desire to measure arterial oxygen saturation ($SaO_2$). Accordingly, most conventionally used pulse oximeters measure $SaO_2$. The device described in WO 94/03102, for example, attempts to address the problem of motion artifact in measuring $SaO_2$ by transmitting into the blood not only n predetermined wavelengths of light, but also an additional wavelength that makes it possible to cancel the motion artifact. Although WO 94/03102 broadly describes the use of a plurality of wavelengths (including the n+1 motion artifact wavelength) the device exemplified uses three wavelengths. However, in practice, the three wavelengths proposed in WO 94/03102 are not sufficient to overcome motion sensitivity.

Yet another factor that reduces the accuracy of non-invasive $SO_2$ monitors is skin pigmentation: Many existing optical devices do not take into account the variations in transmitted light caused by with varying skin colors, which range from fair through brown to black as the concentration of melanin increases. The peak of melanin's absorption spectrum is at roughly 500 nm, decreasing almost linearly with increasing wavelength. Melanin is present in the epidermis; thus, in very high concentrations as is the case in black skin, it can mask the absorption of hemoglobin in the dermis. Even in brown skin, the absorption by melanin is superimposed on that of hemoglobin so that any algorithm which uses the shape of the absorption spectrum to produce an $SO_2$ estimate needs to compensate for this fact.

International Patent Application No WO 00/09004 describes an optical device which is adapted to measure blood oxygen saturation. The device operates by passing light through biological tissue to monitor the transmitted or reflected output signal from a photodetector of this device continuously. However, one difficulty with the device of the prior art is the fact that the use of a limited number of wavelengths as in WO 00/09004 results in a poor signal-to-noise ratio in the detected signal. This reduces the accuracy of the $SO_2$ determination. Further, this limited-wavelength technique is also more prone to ambient interference e.g. fluorescent lighting, etc.

One way to reduce the impact of the factors mentioned above is to measure $SO_2$ invasively. In these applications, light is usually directed into blood by means of catheter-mounted or enclosed optical fibers. The light intensity measured to determine an absorption spectrum for the blood is then usually that of reflected rather than transmitted light. The obvious disadvantage of invasive monitors is the same as for any other invasive device: patient discomfort and the need for great care in positioning the sensor.

Regardless of whether the arrangement used to monitor $SO_2$ is invasive or non-invasive, there is still the problem of converting the measured light spectrum—which comprises intensity values measured at several and sometimes very many wavelengths—into a single, accurate $SO_2$ value, and to do so quickly enough to be useful in real-time, continuous patient monitoring. There is therefore a standing need to improve the accuracy and reliability of $SO_2$ monitors.

SUMMARY OF THE INVENTION

The invention provides a method for determining blood oxygen saturation, and a corresponding system implementation, according to which at least two blood absorption reference spectra are compiled, corresponding to two different levels of oxygenation, over a wavelength range. Light from a light source is then directed into blood of a subject, for example via one or more optical fibers, either invasively or non-invasively. A remitted light absorption spectrum from the blood is then sensed by a detection arrangement. After suitable signal conditioning to provide a digital representation of the remitted spectrum, computer-executable code in a computation software module then computes an oxygen saturation value as a function of the remitted light absorption spectrum relative to the blood absorption reference spectra.

The blood absorption reference spectra and the remitted light absorption spectrum are preferably normalized before the oxygen saturation value is computed. Normalization preferably comprises two main procedures: DC-offsetting of the spectra linearly between two isosbestic wavelengths that lie in the wavelength range; and scaling the DC-offsetted blood absorption reference spectra and the remitted light absorption spectrum by a function of the area under each respective DC-offsetted spectrum between the two isosbestic wavelengths.

The step of computing the oxygen saturation value advantageously comprises computing an optimal value of a cost function that indicates closeness of correspondence between the remitted light absorption spectrum relative to the blood absorption reference spectra. For example, the optimal value can be determined by interpolation of the remitted light absorption spectrum relative to at least two of the blood absorption reference spectra.

As for the reference spectra, at least one minimum blood absorption reference spectrum and one maximum blood absorption reference spectrum are preferably compiled, corresponding to minimum and maximum blood oxygenation values, as well as at least one intermediate blood absorption reference spectrum. Computation of the oxygen saturation value is then done as a function of the remitted light absorption spectrum relative to at least two of the blood absorption reference spectra. One way to do this is for the system to determine the two blood absorption reference spectra that are closest to but are respectively greater than and less than the remitted light absorption spectrum; the oxygen saturation value can then be computed by linear interpolation of the remitted light absorption spectrum relative to the closest blood absorption reference spectra. Another way comprises computing the oxygen saturation value by non-linear interpolation of the remitted light absorption spectrum relative to at least three of the blood absorption reference spectra.

Accuracy of the system may in many cases be improved by further white-balancing the remitted light absorption spectrum and then using the white-balanced remitted light absorption spectrum in the step of computing the an oxygen saturation value.

The light source preferably generates the light directed into the blood from a white-light LED. The spectrum of the white-light LED may then be pre-determined and a representation of the white-light LED spectrum can be stored, for example in a non-volatile medium that can be delivered along with the LED. The remitted light absorption spectrum can then be adjusted as a function of the spectrum of the white-light LED. By storing the white-light LED spectrum permanently, that is, in a non-volatile medium, no further characterization of the light source is needed. This aspect of the invention may also be applied in other medical instruments that require a white-light source, even those that are not intended to measure blood oxygen saturation.

BRIEF DESCRIPTION OF THE DRAWINGS

FIG. 2 is a block diagram of the main hardware and software components of a system that implements the method according to the invention.

DETAILED DESCRIPTION

Figure 1:
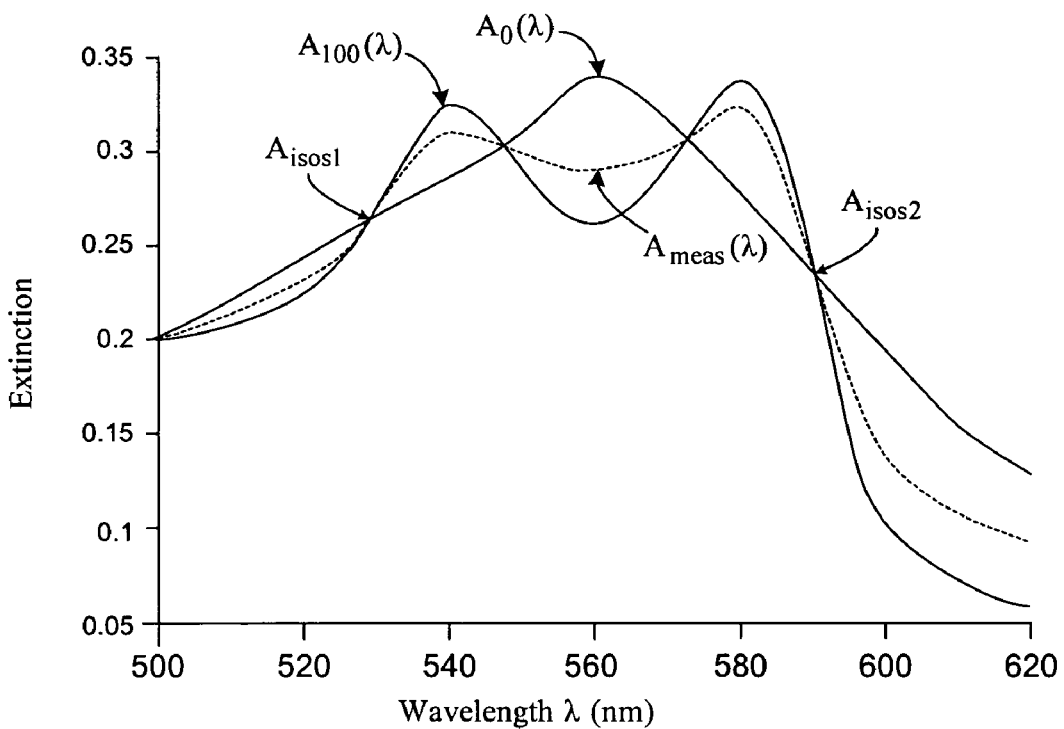
FIG. 1 illustrates different light absorption spectra of blood at different levels of oxygenation.

FIG. 1 illustrates several characteristics of light absorption by blood over a range of wavelengths. In this discussion, $A_x(\lambda)$ represents an absorption spectrum of blood with x % oxygenation whereas $A_y$ represents an absorption value at wavelength y. In FIG. 1, three spectra are illustrated: $A_0(\lambda)$ and $A_{100}(\lambda)$, representing fully deoxygenated and fully oxygenated blood, respectively, and $A_{meas}(\lambda)$, representing an absorption spectrum that is measured in an actual subject using any invasive or non-invasive technique. For all patients, 0<meas<100. In words: the actual $SO_2$ (or $S_aO_2$) value for a patient will always be between 0% and 100%. Given an actual measured absorption spectrum $A_{meas}(\lambda)$, the question then becomes what $S_aO_2$ value the spectrum represents. The way in which the invention determines this is explained below and forms a key aspect of this invention.

As is well known, there are several wavelengths—isosbestic wavelengths—at which the light absorption of hemoglobin is independent of the degree of oxygenation. Five such isosbestic wavelengths are visible in FIG. 1, two of which, at wavelengths 522.7 nm and 586.0 nm, are labeled $A_{523}$ and $A_{586}$, respectively. Other isosbestic wavelengths are 505.9, 548.6, and 569.7 nm, and there are many more. These standard values are usually rounded, and are reported slightly differently in some literature, depending on the test methodology used.

In broadest terms, this invention involves a method and system implementation that: 1) is invasive (inserted in the body, such as on catheters) or non-invasive (such as sensors placed against the skin, finger cuffs, ear lobe clips, etc.); 2) determines, measures, estimates, etc., blood oxygen saturation; 3) by directing multiple wavelengths of light from a light source, especially over the wavelength region of 500-600 nm; 4) into blood in an artery or any other blood vessel or body tissue; 5) to determine a measured absorption, reflectance, or transmission spectrum; 6) that is matched in any manner (least squares or other metric fits, neural networks, "pattern matching," table comparisons, etc.); 7) against two or more reference spectra representing different predetermined levels of blood oxygenation such that the match yields a measure of actual blood oxygen saturation SO2 or SaO2.

FIG. 2 illustrates the main hardware and software components of the invention, which are explained below. Shown without further explanation here are one or more processors 340, system memory 345, and system software (such as an operating system), which perform their well-known tasks, in particular, coordinating and controlling the various hardware devices within the monitor 300, as well as executing the processor-executable code that implements the different software modules described below. Other hardware and software components of a conventional computer will of course also be included in the monitor 300 as needed.

In FIG. 2, both an invasive and a non-invasive implementation is shown for the sake of simplicity; in practice, only the one or the other will normally be used, but FIG. 2 also illustrates the fact that the same monitor 300 according to the invention can be used in either case.

The source of light 301 is preferably broadband with sufficient spectral energy to allow for adequate discrimination and measurement resolution, at least over the wavelength range that includes the five isosbestic wavelengths that lie in the range of 500-600 nm. White light has, by definition, sufficient spectral energy within the visible spectrum in the range of 500-600 nm. Incandescent, fluorescent and halogen bulbs may be used to approximate white light. Greater thermal stability and longer life can usually be obtained by using white-light LEDs, however, and for that reason these solid-state devices are preferred.

Additional advantages of such long-life, white LEDs include: low power requirements, since it is a semiconductor, unlike an incandescent bulb, which generates heat to produce light; b) no ultraviolet (UV) light is generated (long exposure to high intensity UV can produce tissue problems (that is, sunburn); c) no infrared (IR) light is produced (a heat source)—the device stays cool, which contributes to its improved thermal stability; d) as a result of b) and c), all the power required to produce the spectral content of the LED is usable within the wavelength range of interest and, furthermore, no optical filtering is needed to remove unwanted spectral content; e) they are cheap; and f) the respond fast—since LEDs can be turned on and off very fast, they can be pulsed on and off so as to allow dark signal to be removed without the need for a mechanical shutter.

One problem with many conventional LEDs, however, is that their encapsulant yellows over time, which causes shift to longer wavelengths. Some newer LEDs use a silicone gel, however, as an encapsulant; these LEDs typically retain their original transmission spectrum much better over their exceptionally long normal lifespan, which is on the order of hundreds of thousands of hours of operation.

The light is led to the blood either directly and invasively, for example, through one or more optic fibers 111 mounted on or in a catheter 110 to a coupler or lens 100 (which may simply be the end of the transmission fiber), or indirectly and non-invasively, for example, by being conveyed from the source through one or more optic fibers 211 and then being directed against the skin of a patient's finger, etc., using a device 200 such as a finger cuff.

Light that is then remitted by the blood must be detected, and any conventional apparatus may be used to accomplish this. Either dedicated optical fibers 112, 212 may be used to convey the remitted light to the monitor 300, or the transmission fibers 111, 211 may be used as long as suitable time-multiplexing is arranged.

Any known light-detector 302 may be used to measure the blood's absorption spectrum. Some conventional systems use an array of photodetectors, each tuned to the wavelength of a respective one of a plurality of substantially single-wavelength LEDs in the light source 301. As mentioned above, though, the preferred light source is a broadband ("white" source). This avoids the need for separate optical transmission fibers (one per wavelength) and also provides sufficient spectral energy over the wavelength region of interest. In the preferred embodiment of the invention, the detector 302 is a conventional spectrometer that generates the measured spectrum using a diffraction grating and an array of photodetectors.

The signal from the detector 302 must normally be conditioned using known circuitry 304 before being processed digitally. Such conditioning will normally include various forms of filtering, scaling, analog-to-digital conversion, etc. The result of the conditioning will be a conditioned absorption spectrum $A_{cond}(\lambda)$.

As mentioned above, the spectrum of the light source 301 will not be perfectly flat. This will affect the accuracy of the $SO_2$ (or SaO2) calculations: a "dip" in the measured spectrum might have nothing to do with the blood absorption, for example, but rather with a lower-intensity spectral region in the transmitted light. The invention provides different methods for compensating for this deviation from pure "whiteness" in the light source so as to determine the measured absorption spectrum $A_{meas}(\lambda)$.

According to one method for white-balancing, a white-balancing software module 312 calculates $A_{meas}(\lambda)$ according to the formula:

$$A_{meas}(\lambda) = \log_{10} \frac{A_{cond}(\lambda) - D_\lambda}{R_\lambda - D_\lambda}$$

where D is a dark reference intensity at each wavelength $\lambda$ and R is a white reference intensity at each wavelength $\lambda$.

The white and dark reference spectra may be determined using known techniques: Before taking a measurement, the optical sensor (100, 200) is exposed to a standard white reflective surface to give a white reference spectrum. A dark reference spectrum is then also obtained by excluding all excitation light from the optical sensor.

An alternative white-balancing method according to the invention takes advantage of the known spectral stability of modern long-life LEDs: Given one or more such LEDs as the light source, in particular, those with silicone encapsulation, the spectrum of the light source can be measured once, in an initial characterization step, and the parameters of this characterization (after normalization, as described below) can be stored in a non-volatile medium 320 such as an EPROM chip. This chip, or at least the parameters, can be created or determined once, for example by the LED manufacturer as a factory characterization, such that the parameters can be stored with the LED and can be recalled for later use. No further white measurements would then be needed at all. The values of $A_{cond}(\lambda)$ can then be adjusted according to any known balancing algorithm to account for variations in the spectrum of the white-light LED and thus to form $A_{meas}(\lambda)$.

Note that this procedure of pre-characterizing the stable LED, storing its characterizing parameters in a non-volatile, computer-readable medium, and then including this medium along with the product (the LEDs) will also be beneficial in any other medical instrument (that is, even those not related to determining blood oxygenation) that needs a well-defined source of white light for proper or accurate operation: Eliminating the need for continuing characterization will not only simplify the operation of such instruments, but will also improve long-term reliability by eliminating the requirement for potentially error-prone re-characterizations.

Figure 3:
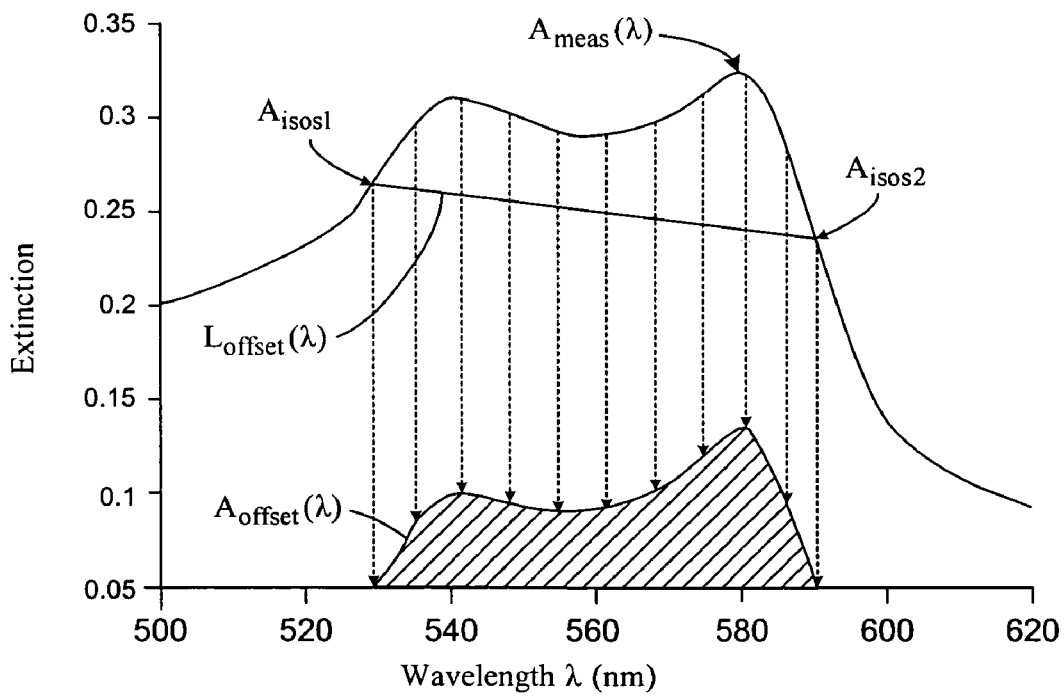
FIG. 3 illustrates a preferred normalization method for absorption spectra.

In the preferred embodiment of the invention, the next step toward estimation of oxygen saturation is normalization of the measured absorption spectrum $A_{meas}(\lambda)$. This preferably involves two different procedures: DC-offsetting and area normalization. See FIG. 3: Assume that one were to draw a line $L_{offset}(\lambda)$ through two of the isosbestic points $A_{isos1}$ and $A_{isos2}$ on the "curve" of the measured absorption spectrum $A_{meas}(\lambda)$. One suitable, but not necessary, choice would be isos1=523 and isos2=586, because they bracket almost the entire wavelength region of interest. Now, for each point on the $A_{meas}(\lambda)$ curve subtract $L_{offset}(\lambda)$ to form a new absorption curve $A_{offset}(\lambda)$. In essence, this brings down the $A_{isos1}$ and $A_{isos2}$ points to the 0-extinction axis, linearly adjusts every value in between and effectively removes the DC offset inherent in the $A_{meas}(\lambda)$ curve.

As a second normalization step, a final normalized measured absorption spectrum $A_{norm}(\lambda)$ is then created by scaling each value of $A_{offset}(\lambda)$ by a function of (and preferably simply by division by) the area under the $A_{offset}(\lambda)$ curve from $\lambda$=isos1 to $\lambda$=isos2. This is the shaded region in FIG. 3. In short, $A_{offset}(\lambda)$ is normalized with respect to its area to give $A_{norm}(\lambda)$. Well known numerical methods may be used to calculate $A_{norm}(\lambda)$ given $A_{meas}(\lambda)$, $A_{isos1}$ and $A_{isos2}$.

Finally, the normalized measured absorption spectrum $A_{norm}(\lambda)$ is compared in a fitting software module 315 with a plurality of reference absorption spectra (stored in numerical form in a memory region or non-volatile storage device 330) to determine a value of $SO_2$ or $S_aO_2$, which may be displayed in any known manner by a display device 500.

As a simple case of how oxygen saturation is determined according to the invention, assume that one uses any technique to determine a minimum and a maximum possible absorption spectrum $A_{min}(\lambda)$ and $A_{max}(\lambda)$. As an extreme example, $A_{min}(\lambda)$ and $A_{max}(\lambda)$ could be $A_0(\lambda)$ and $A_{100}(\lambda)$, respectively. Assume also that $A_{min}(\lambda)$ and $A_{max}(\lambda)$ are normalized in the same manner as was just described. For example, these spectra may be compiled from whole blood samples (measured in a cuvette), or spectra recorded in skin, or the mean spectra recorded from several individuals. As one example of.

As just one simple example, $A_{min}(\lambda)$ and $A_{max}(\lambda)$ may be chosen to be $A_0(\lambda)$ and $A_{100}(\lambda)$, respectively. The fully oxygenated spectrum $A_{100}(\lambda)$ can be obtained by equilibration of whole blood in a cuvette at 37° C., or in the skin of the forefinger heated to 44° C. at maximal reactive hyperemia following release of an inflatable cuff after six minutes of brachial artery occlusion. The fully deoxygenated spectrum $A_0(\lambda)$ can be obtained, for example, by equilibration of whole blood in the cuvette with 95% N, and 5% $CO_2$ at 37° C. or, in skin of the forefinger heated to 44° C. at the end of a six minute period of brachial artery occlusion prior to release of the inflatable cuff. The reference absorption spectra for a given light source can then be compiled using any known spectrometric technique. Of course, any other known laboratory procedure may be followed to determine $A_{min}(\lambda)$ and $A_{max}(\lambda)$ for any given choice of min and max.

Because some form of interpolation between reference spectra is used in the preferred embodiment of the invention for determining what level of oxygenation a given measured absorption spectrum corresponds to, $A_{min}(\lambda)$ and $A_{max}(\lambda)$ are preferably chosen to be less than and greater than, respectively, than all expected measured absorption spectra. The most obvious way to do this, of course, is to choose min=0 and max=100. This choice is not mandatory, however: as long as min and max are neither too great nor too small, respectively, then $A_0(\lambda)$ and $A_{100}(\lambda)$ could be determined by extrapolation from the $A_{min}(\lambda)$ and $A_{max}(\lambda)$ spectra actually measured in vitro. For greater accuracy, such extrapolation should preferably include at least one intermediate reference spectrum (see below).

$A_{norm}(\lambda)$ will fall between the two "extreme" absorption profiles, (either the experimentally determined $A_{min}(\lambda)$ and $A_{max}(\lambda)$, or $A_0(\lambda)$ and $A_{100}(\lambda)$, and in almost all cases, both) as shown in FIG. 1 (in non-offset and unnormalized form). The question is then how oxygenated the actual blood is. It is somewhere between min % and max %, but where? One way to answer this question is to use a simple table look-up with $A_x(\lambda)$ entries for a range of values of x, for example, every 1%, which may be computed using normal interpolation and stored in advance. Another procedure is to use well-known numerical methods to find the linear combination of the minimum and maximum oxygenation reference spectra $A_{min}(\lambda)$ and $A_{max}(\lambda)$ that "best" matches $A_{norm}(\lambda)$ in some sense, such as least-squares. In short, which value $\alpha$ ($0<\alpha<1$) gives the best match between $A_{norm}(\lambda)$ and $[\alpha \cdot A_{min}(\lambda)+(1-\alpha) A_{max}(\lambda)]$ over the range of wavelengths? This can be determined, again using known numerical techniques, by finding the value $\alpha$ that minimizes the cost function:

$$\text{SUM } \{A_{norm}-[\alpha \cdot A_{min}+(1-\alpha) A_{max}]\}^2 \lambda$$

Of course, other measures of closeness (other cost functions) of match could be used instead of least squares, and any of the many available numerical optimization methods maybe used to optimize $\alpha$ (just a couple examples: gradient descent, Newton-Raphson). The optimum value of $\alpha$ also yields the degree (percentage) of oxygenation, which will be =[$\alpha \cdot$max+ (1-$\alpha$)min].

One disadvantage of this simple method, which amounts to linear interpolation between $A_{min}(\lambda)$ and $A_{max}(\lambda)$, is that it is known that actual absorption profiles do not vary linearly between the extremes. This non-linearity introduces inaccuracy in the estimate of oxygenation.

In the preferred embodiment of the invention, more than two reference spectra are compiled, that is, not only $A_{min}(\lambda)$ and $A_{max}(\lambda)$, but also at least one intermediate reference spectrum $A_{inter}(\lambda)$, whose (preferably normalized) parameters are stored in the component 330 along with the (also preferably normalized) parameters for $A_{min}(\lambda)$ and $A_{max}(\lambda)$. Such an intermediate spectrum can be determined in vitro in the same way as described above. There are different ways to determine the percentage of oxygenation given at least one intermediate reference spectrum. The simplest way is to determine whether $A_{norm}(\lambda)$ lies (wholly or at least mostly) between $A_{min}(\lambda)$ and $A_{inter}(\lambda)$, or between $A_{inter}(\lambda)$ and $A_{max}(\lambda)$ and then to apply the linear interpolation technique described above, but just within the bracketed range.

This method of bracketing followed by linear interpolation may be applied quickly even where many intermediate reference spectra are compiled. Note that it is not necessary for the reference spectra to be evenly spaced (in terms of degree of oxygenation). It is thus also not necessary to ensure that the degree of oxygenation of the reference spectra are whole numbers. Rather, a possibly large set of blood samples can be obtained; their degrees of oxygenation can be determined in vitro; and the samples' absorption spectra, possibly grouped according to other factors than oxygenation alone, can then be stored and used for actual $SO_2$ determination.

As an alternative, given two extreme reference spectra and one intermediate reference spectrum, a best-fit approximation of the normalized measured absorption spectrum $A_{norm}(\lambda)$ can be computed to the second-order (quadratic) surface (polynomial) that passes through all three reference spectra. In essence, determination of $SO_2$ then becomes, mathematically, equivalent to determining where on the second-order surface $A_{norm}(\lambda)$ most closely lies. Of course, given even more reference spectra, higher-order reference surfaces can be computed, with the cost function used to determine $SO_2$ being evaluated for a best-fit (in any chosen sense) with respect to $A_{norm}(\lambda)$.

Two of the advantages of the invention are: There is no requirement for the user to calibrate the system; and since the $SO_2$ determination is made by spectral recognition and spectral comparison with the reference spectra, the method is not prone to interference from patient movement. In the technique according to the invention, interference from patient movement will affect only certain wavelengths in the 500 to 600 nm range. These movement artifacts at particular wavelengths affect the quality of the fit between the measured spectrum and the stored reference spectrum, but otherwise have little influence on the spectral recognition and comparison processes which ultimately determine the $SO_2$. The technique is, therefore, insensitive to patient movement.

Although the light source preferably generates white light—for reasons explained—the invention's method of computing the oxygenation value by evaluating a cost function of the remitted absorption spectrum relative to at least two reference spectra could also be used in implementations that transmit discrete wavelengths of light, for example from an array of single-wavelength LEDs, as long as enough wavelengths are included to allow for compilation of a reasonable representation of the remitted spectrum, and at least two of the wavelengths are isosbestic such that they can be used in the spectral normalization procedure.

What is claimed is:

1. A method for determining blood oxygen saturation comprising:
   compiling at least two blood absorption reference spectra, corresponding to two different levels of oxygenation, over a wavelength range;
   directing light into the blood of a subject;
   sensing a remitted light absorption spectrum from the blood;
   compiling at least one minimum blood absorption reference spectrum and one maximum blood absorption reference spectrum corresponding to minimum and maximum blood oxygenation values, as well as at least one intermediate blood absorption reference spectrum; and
   computing an oxygen saturation value as a function of the remitted light absorption spectrum relative to at least two of the blood absorption reference spectra.

2. A method as in claim 1, further comprising normalizing the blood absorption reference spectra and the remitted light absorption spectrum before computing the oxygen saturation value.

3. A method as in claim 2, in which the step of normalizing the blood absorption reference spectra and the remitted light absorption spectrum includes DC-offsetting the spectra linearly between two isosbestic wavelengths that lie in the wavelength range.

4. A method as in claim 3, in which the step of normalizing the blood absorption reference spectra and the remitted light absorption spectrum includes scaling the DC-offsetted blood absorption reference spectra and the remitted light absorption spectrum by a function of the area under each respective DC-offsetted spectrum between the two isosbestic wavelengths.

5. A method as in claim 1 in which the step of computing the oxygen saturation value comprises computing an optimal value of a cost function that indicates closeness of correspondence between the remitted light absorption spectrum relative to the blood absorption reference spectra.

6. A method as in claim 5, in which the step of computing the optimal value comprises interpolation of the remitted light absorption spectrum relative to at least two of the blood absorption reference spectra.

7. A method as in claim 1, further comprising:
   determining the two blood absorption reference spectra that are closest to but are respectively greater than and less than the remitted light absorption spectrum; and
   computing the oxygen saturation value by linear interpolation of the remitted light absorption spectrum relative to the closest blood absorption reference spectra.

8. A method as in claim 1, further comprising computing the oxygen saturation value by non-linear interpolation of the remitted light absorption spectrum relative to at least three of the blood absorption reference spectra.

9. A method as in claim 1, further comprising white-balancing the remitted light absorption spectrum and then using the white-balanced remitted light absorption spectrum in the step of computing the oxygen saturation value.

10. A method as in claim 1, further comprising:
    generating the light directed into the blood from a white-light LED;
    pre-determining the spectrum of the white-light LED;
    storing a representation of the white-light LED spectrum; and
    adjusting the remitted light absorption spectrum as a function of the spectrum of the white-light LED.

11. A method as in claim 10, further comprising storing the representation of the white-light LED spectrum permanently, whereby no further characterization of the light source is needed.

12. A system for determining blood oxygenation saturation comprising:
    at least one processor;
    a storage device storing parameters numerically representing at least two blood absorption reference spectra, corresponding to two different levels of oxygenation, over a wavelength range wherein the storage device contains parameters numerically representing at least one minimum blood absorption reference spectrum and one maximum blood absorption reference spectrum corresponding to minimum and maximum blood oxygenation values, as well as at least one intermediate blood absorption reference spectrum;
    a light source generating a spectrum of light over at least the wavelength range;
    a light transmission arrangement directing the generated light from the light source into the blood of a subject;
    a light detection arrangement sensing a remitted light absorption spectrum from the blood;
    conditioning circuitry converting the detected remitted light into a numerically represented, measured remitted absorption spectrum; and
    a computation software module comprising processor-executable code for computing an oxygen saturation value as a function of the remitted light absorption spectrum relative to at least two of the blood absorption reference spectra.

13. A system as in claim 12, further comprising, as part of the computation software module, a normalization sub-module comprising processor executable code for normalizing the blood absorption reference spectra and the remitted light absorption spectrum before computing the oxygen saturation value.

14. A system as in claim 13, in which the normalization sub-module comprises further processor-executable code for DC-offsetting the spectra linearly between two isosbestic wavelengths that lie in the wavelength range.

15. A system as in claim 14, in which the normalization sub-module comprises further processor-executable code for scaling the DC-offsetted blood absorption reference spectra and the remitted light absorption spectrum by a function of the area under each respective DC-offsetted spectrum between the two isosbestic wavelengths.

16. A system as in claim 12, the computation software module further including a fitting sub-module comprising processor-executable code for computing an optimal value of a cost function that indicates closeness of correspondence between the remitted light absorption spectrum relative to the blood absorption reference spectra.

17. A system as in claim 16, further comprising, as part of the computation software module, a fitting sub-module comprising processor-executable code for interpolating the remitted light absorption spectrum relative to at least two of the blood absorption reference spectra.

18. A system as in claim 12, in which the computation software module further comprises processor-executable code:
   for determining the two blood absorption reference spectra that are closest to but are respectively greater than and less than the remitted light absorption spectrum; and
   for computing the oxygen saturation value by linear interpolation of the remitted light absorption spectrum relative to the closest blood absorption reference spectra.

19. A system as in claim 12, in which the computation software module further comprises processor-executable code for computing the oxygen saturation value by non-linear interpolation of the remitted light absorption spectrum relative to at least three of the blood absorption reference spectra.

20. A system as in claim 12, further comprising, as part of the computation software module, a white-balancing sub-module comprising processor-executable code for white-balancing the remitted light absorption spectrum and for passing the white-balanced remitted light absorption spectrum as input to the computation software module for computing the oxygen saturation value.

21. A system as in claim 12, in which:
   the light source includes at least one stable, white-light LED; and
   the storage device includes a storage medium storing predetermined parameters characterizing the spectrum of the white-light LED, the characterizing parameters forming an input to the computation software module useful for adjusting the remitted light absorption spectrum as a function of the spectrum of the white-light LED.

22. A system as in claim 21, in which the storage medium is non-volatile.

23. A method for determining blood oxygen saturation comprising:
   compiling at least one minimum blood absorption reference spectrum and one maximum blood absorption reference spectrum corresponding to minimum and maximum blood oxygenation values, as well as at least one intermediate blood absorption reference spectrum, over a wavelength range each reference spectrum corresponding to a respective level of oxygenation;
   directing light into the blood of a subject;
   sensing a remitted light absorption spectrum from the blood;
   normalizing the blood absorption reference spectra and the remitted light absorption spectrum before computing the oxygen saturation value, the normalization including:
   DC-offsetting the spectra linearly between two isosbestic wavelengths that lie in the wavelength range; and
   scaling the DC-offsetted blood absorption reference spectra and the remitted light absorption spectrum by a function of the area under each respective DC-offsetted spectrum between the two isosbestic wavelengths;
   computing an oxygen saturation value as a function of the remitted light absorption spectrum relative to the blood absorption reference spectra, the computation including:
   computing an optimal value of a cost function that indicates closeness of correspondence between the remitted light absorption spectrum relative to the blood absorption reference spectra; and
   interpolation of the remitted light absorption spectrum relative to at least two of the blood absorption reference spectra; and
   computing the oxygen saturation value as a function of the remitted light absorption spectrum relative to at least two of the blood absorption reference spectra.

24. A system for determining blood oxygenation saturation comprising:
   a least one processor;
   a storage device storing parameters numerically representing at least one minimum blood absorption reference spectrum and one maximum in blood absorption reference spectrum corresponding to minimum and maximum blood oxygenation values, as well as at least one intermediate blood absorption reference spectrum, each reference spectrum corresponding to respective, different levels of oxygenation, over a wavelength range;
   a light source generating a spectrum of light over at least the wavelength range;
   a light transmission arrangement directing the generated light from the light source into the blood of a subject;
   a light detection arrangement sensing a remitted light absorption spectrum from the blood;
   conditioning circuitry converting the detected remitted light into a numerically represented, measured remitted absorption spectrum;
   a computation software module including:
   a normalization sub-module comprising processor-executable code for normalizing the blood absorption reference spectra and the remitted light absorption spectrum before computing the oxygen saturation value by
   DC-offsetting the spectra linearly between two isosbestic wavelengths that lie in the wavelength range; and
   scaling the DC-offsetted blood absorption reference spectra and the remitted light absorption spectrum by a function of the area under each respective DC-offsetted spectrum between the two isosbestic wavelengths; and
   a fitting sub-module comprising processor-executable code for interpolating the remitted light absorption spectrum relative to at least two of the blood absorption reference spectra;
   the computation software module comprising processor-executable code for computing the oxygen saturation value as a function of the interpolation.

* * * * *

UNITED STATES PATENT AND TRADEMARK OFFICE
CERTIFICATE OF CORRECTION

PATENT NO. : 7,400,918 B2
APPLICATION NO. : 10/950257
DATED : July 15, 2008
INVENTOR(S) : Parker Dawood and Michael J. Higgins It is certified that error appears in the above-identified patent and that said Letters Patent is hereby corrected as shown below:

On the first page of the patent, the follow items need correcting:

In the Related U.S. Application Data section, please correct the paragraph to read as follows:

Continuation-In-Part (CIP) of co-pending U.S. Patent Application No. 09/743,206, filed March 15, 2002, incorporated herein by reference, and now U.S. Patent No. 6,990,365, which is a national stage application claiming priority of International (PCT) Patent Application No. PCT/GB99/02127, filed July 2, 1999, which in turn claims priority of Great Britain Patent Application No. 9825243.0, filed November 19, 1998, Great Britain Patent Application No. 9824899.0, filed November 13, 1998, and Great Britain Patent Application No. 9814464.5, filed July 4, 1998, each of which are herein incorporated by reference.

U.S. Patent No. 7,400,918 also claims priority to and is a CIP of co-pending U.S. Patent Application No. 09/762,923, filed April 16, 2001, now U.S. Patent No. 6,842,635, which is a national stage application claiming priority of International Patent Application No. PCT/GB99-02510, filed July 30, 1999, which in turn claims priority of both Great Britain Patent Application No. 9817552.4, filed August 13, 1998 and Great Britain Patent Application No. 9904232.7, filed February 25, 1999, each of which are herein incorporated by reference, U.S. Patent No. 7,400,918 also claims priority to GB Patent Application No. 0322545.5 filed September 26, 2003.

Signed and Sealed this

Twenty-seventh Day of October, 2009

David J. Kappos
*Director of the United States Patent and Trademark Office*